United States Patent
Ponticello et al.

[11] Patent Number: 5,453,424
[45] Date of Patent: Sep. 26, 1995

[54] FURANODIAZEPINES

[75] Inventors: Gerald S. Ponticello, Lansdale; John J. Baldwin, Gwynedd Valley; David C. Remy, North Wales, all of Pa.

[73] Assignee: Merck & Co., Inc., Rahway, N.J.

[21] Appl. No.: 156,343

[22] Filed: Nov. 22, 1993

[51] Int. Cl.⁶ .............. A61K 31/55; C07D 491/048; C07D 491/147
[52] U.S. Cl. .......... 514/221; 540/503; 540/560; 514/220; 548/532; 548/533; 548/536; 548/537; 548/539; 548/540
[58] Field of Search ............... 540/503; 514/221

[56] References Cited

U.S. PATENT DOCUMENTS

| | | | |
|---|---|---|---|
| 4,775,671 | 10/1988 | Hunkeler et al. | 514/220 |
| 4,992,437 | 2/1991 | Naka et al. | 540/503 |

FOREIGN PATENT DOCUMENTS

| | | | |
|---|---|---|---|
| 3223290 | 10/1991 | European Pat. Off. | 504/503 |
| 93/15059 | 8/1993 | WIPO . | |

OTHER PUBLICATIONS

Sanguinetti et al., Two Components Of Cardia Delayed Rectifier K+ Agents, J. Gen. Physiol., Jul., 1990, pp. 195–215.

Hondeghem, Development Of Class III Antiarrhythmic Agents, J. Cardiovasc. Pharmacol, 1992, vol. 20, (Supple. 2), pp. S17–S22.

*Primary Examiner*—Emily Bernhardt
*Attorney, Agent, or Firm*—Sylvia A. Ayler; Francis P. Bigley; Mark R. Daniel

[57] ABSTRACT

This invention is concerned with novel compounds represented by structural formulae I and II.

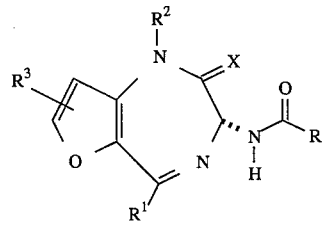

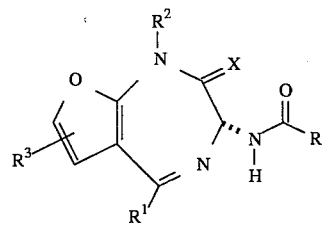

which are useful in the treatment of cardiac arrhythmia.

5 Claims, No Drawings

FURANODIAZEPINES

BACKGROUND OF THE INVENTION

Arrhythmias often occur as complications to cardiac diseases such as myocardial infarction and heart failure. In a serious case, arrhythmias give rise to a ventricular fibrillation and can cause sudden death.

Though various antiarrhythmic agents are now available on the market, those, having both satisfactory effects and high safety, have not been obtained. For example, antiarrhythmic agents of Class I according to the classification of Vaughan-Williams which cause a selective inhibition of the maxima velocity of the upstroke of the action potential (Vmax) are inadequate for preventing ventricular fibrillation. In addition, they have problems regarding safety, namely, they cause a depression of the myocardial contractility and have a tendency to induce arrhythmias due to an inhibition of the impulse conduction. Beta-adrenoceptor blockers and calcium antagonists which belong to Class II and IV respectively, have a defect that their effects are either limited to a certain type of arrhythmia or are contraindicated because of their cardiac depressant properties in certain patients with cardiovascular disease. Their safety, however, is higher than that of the antiarrhythmic agents of Class I.

Antiarrhythmic agents of Class III are drugs which cause a selective prolongation of the duration of the action potential without a significant depression of the Vmax. Drugs in this class are limited. Examples such as sotalol and amiodarone have been shown to possess Class III properties. Sotalol also possesses Class II effects which may cause cardiac depression and be contraindicated in certain susceptible patients. Also, amiodarone is severely limited by side effects. Drugs of this class are expected to be effective in preventing ventricular fibrillations. Pure Class III agents, by defination, are not considered to cause myocardial depression or an induction of arrhythmias due to the inhibition of the action potential conduction as seen with Class I antiarrhythmic agents.

SUMMARY OF THE INVENTION

This invention is concerned with novel compounds represented by structural formulae I and II.

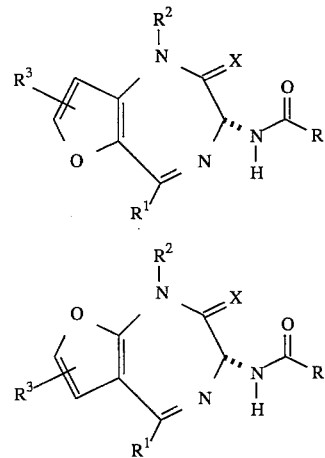

or a pharmaceutically acceptable salt, hydrate or crystal form thereof, the racemic mixture or the individual enantiomers, the diastereomeric mixture, pure diastereomer or enantiomers thereof wherein:

R is $C_1$ to $C_6$ alkyl, $C_1$ to $C_6$ alkylaryl wherein the aryl ring is unsubstituted or substituted with $C_1$–$C_6$ alkyl, $C_1$–$C_6$ alkoxy, hydroxy $C_1$–$C_6$ alkyl, $NR^5R^6$ $C_1$–$C_6$ alkyl, halo, $NR^5R^6$, or hydroxy; $C_1$–$C_6$ alkyl substituted with cycloalkyl $C_3$–$C_8$,

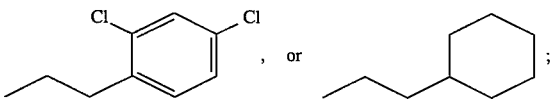

$R^1$ is $C_1$ to $C_6$ alkyl, either straight or branched chain, $C_1$ to $C_6$ substituted alkyl, $C_1$ to $C_6$ alkylaryl, aryl, substituted aryl wherein the aryl ring is unsubstituted or substituted with $C_1$–$C_6$ alkyl, $C_1$–$C_6$ alkoxy, hydroxy, hydroxy $C_1$–$C_6$ alkyl, $NR^5R^6C_1$–$C_6$ alkyl, halo, $NR^5R^6$; heterocyclic; $NR^5R^6$;

$R^2$ is H, $C_1$ to $C_6$ alkyl, either straight or branched chain, or alkylamine; X is O; or in the alternative, $R^2$ and X can be joined to form a heterocyclic ring including imidazoline, imidazole or triazole either substituted with $C_1$–$C_6$ or unsubstituted;

$R^3$ is unsubstituted $C_1$–$C_6$ alkyl, $C_1$–$C_6$ alkoxy, $NO_2$, cyano, COOH, or $COOC_1$–$C_6$ alkyl, $NR^5R^6$, or substituted $C_1$–$C_6$ alkyl wherein the substitution is hydroxy, $C_1$–$C_6$ alkoxy, $NR^5R^6$;

$R^5$ and $R^6$ are independently hydrogen or $C_1$–$C_6$ alkyl or in the alternative, $R^5$ and $R^6$ can be joined to form a 5 or 6 membered ring, which are useful as antiarrhythmic agents. The invention is also concerned with pharmaceutical formulations comprising one of the novel compounds as an active ingredient.

The invention is also concerned with a method of treating arrhythmia by the administration of one of the novel compounds or formulation thereof to a patient in need of such treatment.

DETAILED DESCRIPTION OF THE INVENTION

The novel compounds of this invention have structural formulae I and II:

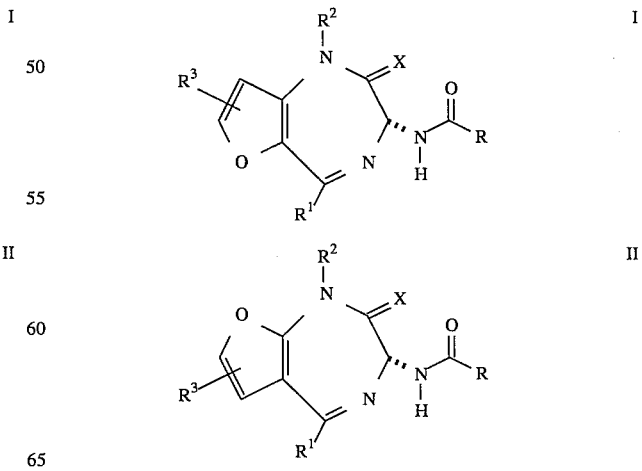

or a pharmaceutically acceptable salt, hydrate or crystal form thereof, the racemic mixture or the individual enanti5omers, the diastereomeric mixture, pure diastereomer or enantiomers thereof wherein:

R is $C_1$ to $C_6$ alkyl, $C_1$ to $C_6$ alkylaryl wherein the aryl ring is unsubstituted or substituted with $C_1$-$C_6$ alkyl, $C_1$-$C_6$ alkoxy, hydroxy $C_1$-$C_6$ alkyl, $NR^5R^6$ $C_1$-$C_6$ alkyl, halo, $NR^5R^6$, or hydroxy; $C_1$-$C_6$ alkyl substituted with cycloalkyl $C_3$-$C_8$,

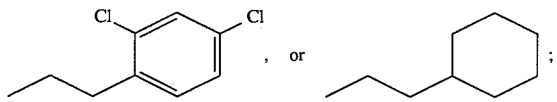

$R^1$ is $C_1$ to $C_6$ alkyl, either straight or branched chain, $C_1$ to $C_6$ substituted alkyl, $C_1$ to $C_6$ alkylaryl, aryl, substituted aryl wherein the aryl ring is unsubstituted or substituted with $C_1$-$C_6$ alkyl, $C_1$-$C_6$ alkoxy, hydroxy, hydroxy $C_1$-$C_6$ alkyl, $NR^5R^6$ $C_1$-$C_6$ alkyl, halo, $NR^5R^6$;heterocyclic; $NR^5R^6$;

$R^2$ is H, $C_1$ to $C_6$ alkyl, either straight or branched chain, or alkylamine; X is O; or in the alternative, $R_2$ and X can be joined to form a heterocyclic ring including imidazoline, imidazole or triazole either substituted with $C_1$-$C_6$ or unsubstituted;

$R^3$ is unsubstituted $C_1$-$C_6$ alkyl, $C_1$-$C_6$ alkoxy, $NO_2$, cyano, COOH, or $COOC_1$-$C_6$ alkyl, $NR^5R^6$, or substituted $C_1$-$C_6$ alkyl wherein the substitution is hydroxy, $C_1$-$C_6$ alkoxy, $NR^5R^6$; $R^5$ and $R^6$ are independently hydrogen or $C_1$-$C_6$ alkyl or in the alternative, $R^5$ and $R^6$ can be joined to form a 5 or 6 membered ring.

The pharmaceutically acceptable salts of the compounds of Formula I include the conventional non-toxic salts or the quaternary ammonium salts of the compounds of Formulae I and II formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glucolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formulae I and II which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

One embodiment of the novel compounds of this invention can be represented by the structure

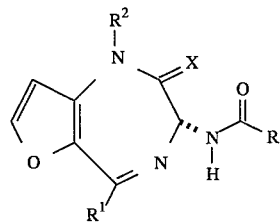

Specifically exemplifying the novel compounds of this invention are those in which R is either

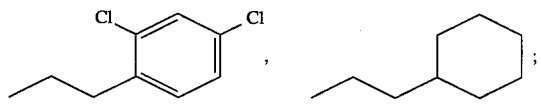

$R^1$ is phenyl, $R^2$ is methyl and X is O. The preparation of compounds of this type is presented in Example 1 and represented schematically in Scheme I.

SCHEME I

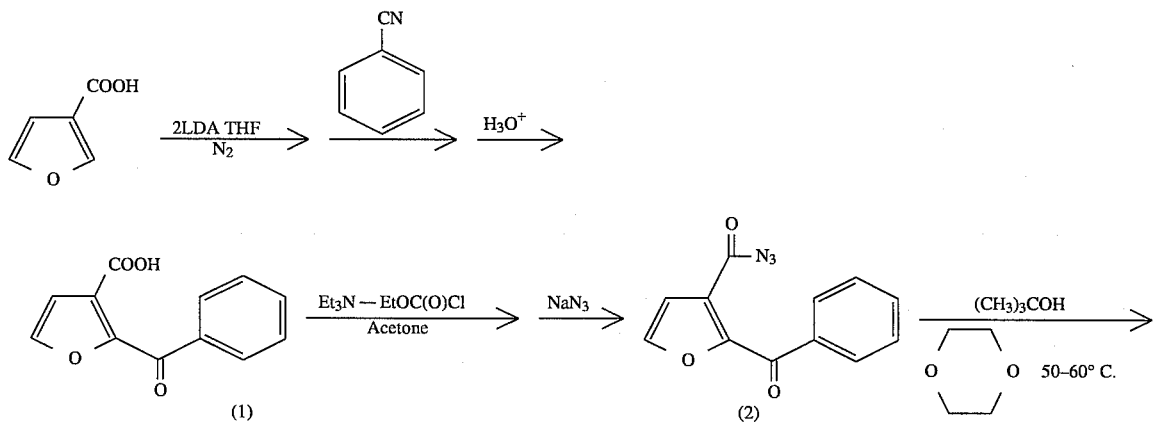

-continued
SCHEME I
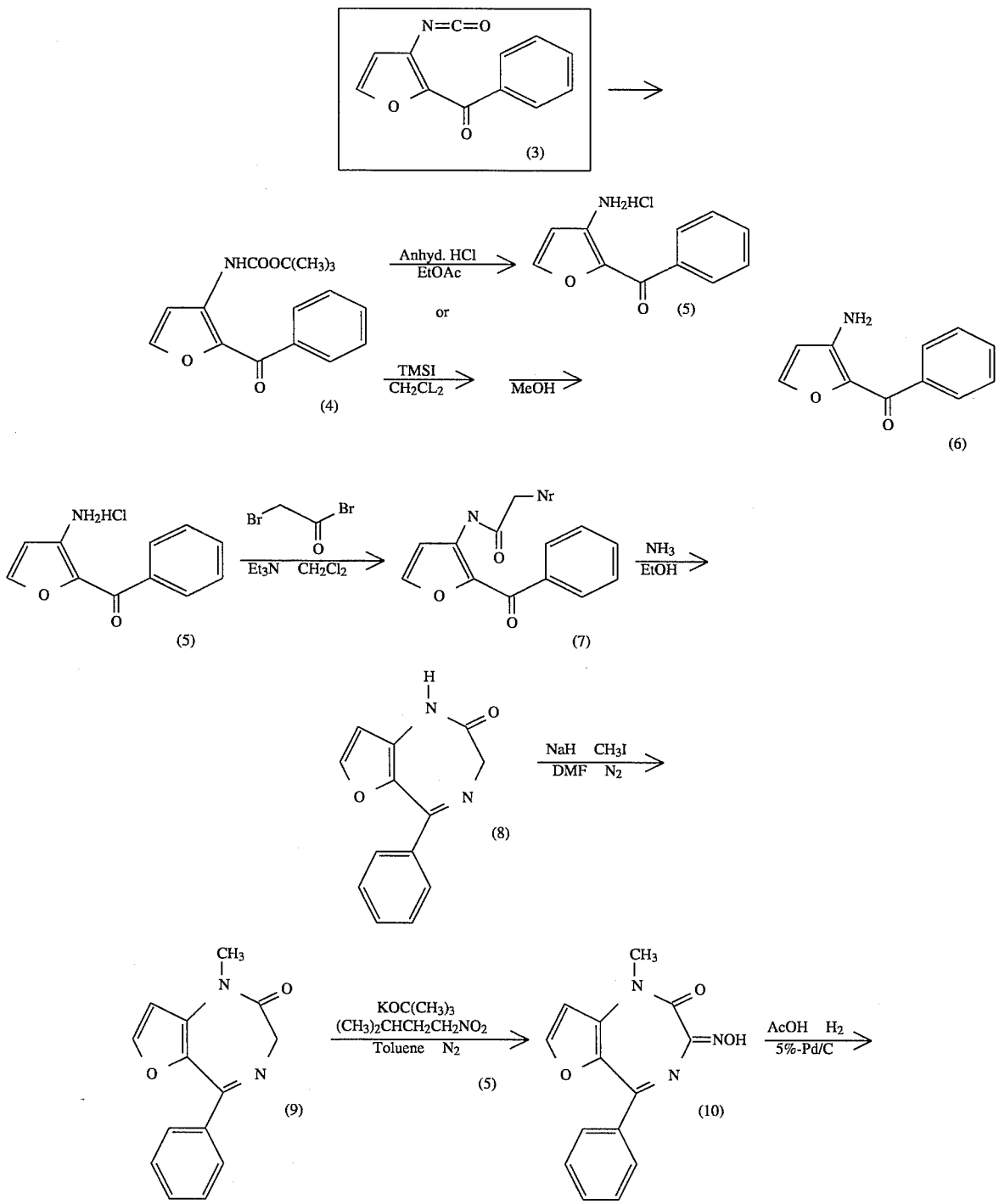

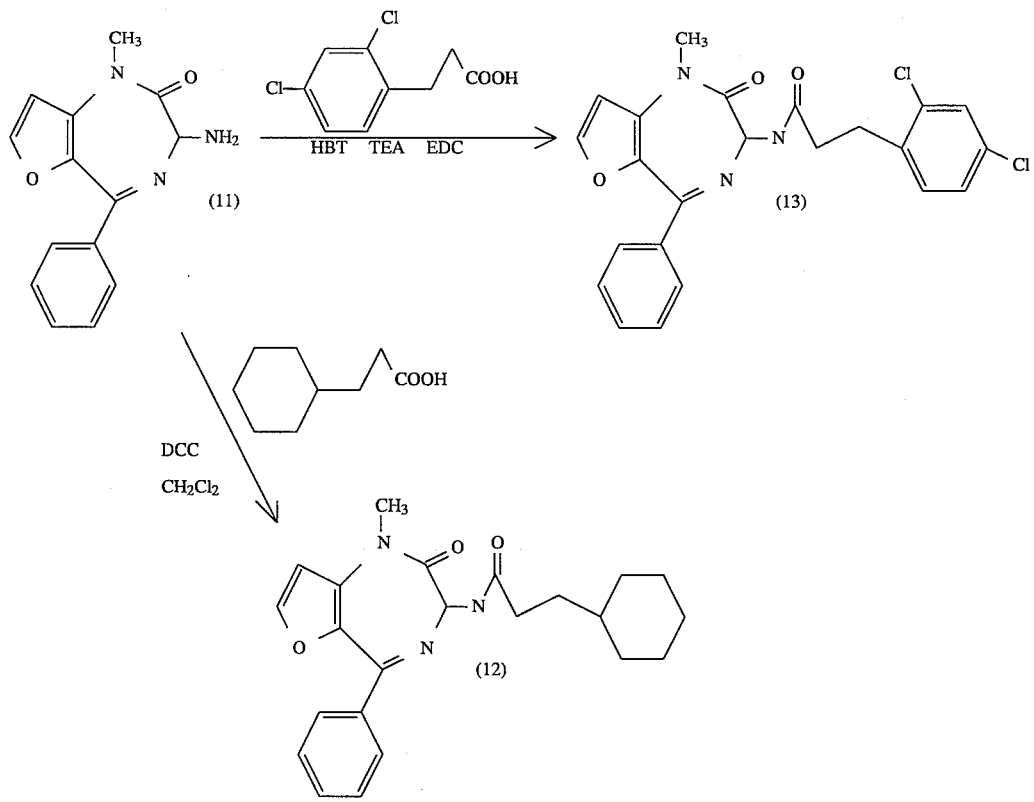

EXAMPLE I

The synthesis outlined in Scheme I is further defined as follows: (Note, the number preceeding the name in parenthesis corresponds to the structure in the scheme.)

(1) 2-Benzoyl-3-furoic acid

Lithium diisopropyl amide (276 mL, 0.4 mol of a 1.5M cyclohexane solution) was added dropwise over 45 minutes under nitrogen atmosphere at −78° C. to −55° C. to a stirred solution of 3-furoic acid (22.4 g, 0.2 mol) in tetrahydrofuran (70 mL). After one hour, the temperature was raised to −10° C. for ½ hour. The yellow solution was recooled to −78° C. and benzonitrile (20.6 g, 0.2 mol) was added over ¼ hour. After one hour at −78° C., the temperature was brought to 0° C. over 2½ hours. Following a one hour period at 0° C., the reaction was diluted with cold water (200 mL). The tetrahydrofuran was removed in vacuo. The residue was acidified with hydrochloric acid to pH 5 and was left at room temperature overnight. The x s mixture was further acidified to pH 3 and the precipitated tan solid was extracted into ether (600 mL). The ether extract was washed with saturated NaCl solution, dried over Na$_2$SO$_4$, filtered and concentrated in vacuo. The product (26.0 g) was recrystallized from n-butyl chloride (100mL) and petroleum ether (100 mL). Weight of light tan solid recovered was 20.5 g.

(2) 2-Benzoyl-3-furoyl azide

2-Benzoyl-3-furoic acid (27 g, 0.125 mol) was dissolved in dry acetone (500 mL). The solution was cooled to 0° C. under a nitrogen atmosphere and triethylamine (20.9 mL, 0.15 mol) was added, followed by ethyl chloroformate (15.3 mL, 0.16 mol). The mixture was stirred for ¾ hours at 0° C. and a solution of sodium azide (13.65 g, 0.21 mol) in water (50 mL) was added. After one hour, the solid mixture was diluted with water (50 mL) and the acetone was removed in vacuo at room temperature. The residual oil-water mixtue was extracted with ethyl acetate (250 mL). The combined extracts were washed with saturated NaCl solution, dried over Na$_2$SO$_4$, filtered and concentrated in vacuo to give a quantitative yield (30 g) of the acylazide as a red liquid. This material was used in the neutralization reaction without purification.

(4) t-Butyl (2-benzoylfuran-3-yl)carbamate

2-Benzoyl-3-furoyl azide (30 g, 0.125 mol) was dissolved in 1,4-dioxane (100 mL) and t-butyl alcohol (14 mL) was added. The mixture was heated in an oil bath at 60° C. under nitrogen for four hours until the evolution of nitrogen ceased. Then it was poured into ice water (400 mL) and the product was extracted with ethyl acetate (300 mL). The extract was washed with saturated NaCl solution, dried over Na$_2$SO$_4$, filtered and concentrated in vacuo. A viscous brown liquid was obtained (30.2 g).

(5 or 6.) 3-Amino-2-benzoylfuran

Two procedures have been used to produce this intermediate. These are described herein as Method A and Method B.

Method A: t-Butyl (2-benzoylfuran-3-yl)carbamate (30.1 g, 0.105 mol) was dissolved in ethyl acetate (300 mL) and the solution was cooled to 0° C. and was saturated with anhydrous hydrogen chloride gas. The mixture was left overnight as the temperature rose to ambient conditions. Next, the mixture was concentrated in vacuo to remove the excess hydrogen chloride. The residual solid was taken up in ethyl acetate (200 mL)

and saturated sodium bicarbonate (200 mL). The ethyl acetate solution was filtered through activated carbon and the yellow filtrate was dried over sodium sulfate, filtered and concentrated in vacuo to a yellow solid (15.5 g).

Method B: t-Butyl (2-benzoylfuran-3yl)carbamate (100 g, 0.348 mmol) was dissolved in chloroform (1 mL). The solution was cooled to 0° C. and trimethylsilyl iodide (83.6 mg, 0.418 mmol) was added under nitrogen. The reaction was stirred for 10 minutes and then was concentrated to drynes in vacuo. The residue was suspended in ether (3 mL) and methanol (0.07 mL) was added to form a solution. Concentration of the solution in vacuo gave product which was identical to the product obtained in Method A.

(7) 3-(2-Bromoacetamido)-2-benzoylfuran

3-Amino-2-benzoylfuran (4.93 g, 0.025 mol) was dissolved in s dry methylene chloride (50 mL). The solution was cooled to 0° C. under nitrogen and triethylamine (3.8 mL, 0.0275 mol) was added followed by bromoacetyl bromide (2.4 mL, 0.0275 mol). The mixture was stirred at 0° C. for five hours. Next another 10% of triethylamine and bromoacetyl bromide were added and the reaction was left over night. Ehtyl acetate (200 mL) and saturated NaCl (75 mL) were added. The ethyl acetate layer was separated, washed with saturated NaCl solution, dried over sodium sulfate, filtered and concentrated in vacuo. A tan solid was obtained in theoretical yield (7.7 g).

(8) 2,3-Dihydro-2-oxo-5-phenyl-1H-1,4-furo[3,2-e]diazepine

Absolute ethanol (50 mL) was saturated with anhydrous ammonia gas at 0° C. To this solution was added dropwise over 5 minutes, 3-(2-bromoacetamido)-2-benzoylfuran (7.7 g, 0.025 mol) dissolved in tetrahydrofuran (25 mL). Next the reaction flask was sealed and left over night at ambient temperature. The reaction mixture was concentrated in vacuo to remove the excess ammonia. The residue was dissolved in ethanol (100 mL) and 3A molecuar sieves were added (5 g). The mixture was heated at reflux until cyclization was essentially complete (5 hours). The molecular sieves were removed by filtration and the ethanol was removed in vacuo. The residual solid was taken up in ethyl acetate (500 ml) and water (150 mL). The ethyl acetate extract was washed with satuated NaCl solution, dried over sodium sulfate, filtered and concentrated in vacuo to a brown solid (8.4 g). Chromatography on silica gel, using ethyl acetate, gave 3.14 g of pure product, mp 220 222° C.

(9) 2,3-Dihydro-1-methyl-2-oxo-5-phenyl-1H-1,4-furo[3,2-e]diazepine

Under a nitrogen atmosphere, 60% sodium hydride in mineral oil (0.64 g, 0.016 mol) was washed free of mineral oil with dry hexane. Then a solution of 2,3-dihydro-2-oxo-5-phenyl-1H-1,4-furo[3,2-e]diazepine (3.11 g, 0.0138 mol) in dry dimethylformamide (2.5 mL) was added with ice-bath cooling. After ½ hour, methyl iodide (2.37 g, 0.0166 mol) was added. After 1 hour at ambient temperatue, the dimethyfformamide was removed in vacuo. The residue was taken up in ethyl acetate (100 mL) and 1N HCl (25 mL). The mixture was neutralized with sodium bicarbonate and the ethyl acetate solution was separated, washed with saturated NaCl, dried over sodium sulfate, filtered and concentrated in vacuo. An amber oil was obtained which solidified upon standing. (3.31 g).

(10) 2,3-Dihydro-1-methyl-3-oximido-5-phenyl-1H-1,4-furo[3,2-e] diazepin-2-one

A solution of 2,3-dihydro-1-methyl-5-phenyl-1H-1,4-furo[3,2-e] diazepin-2-one (2.90 g, 0.012 mol) in dry toluene (70 ml) was cooled to −10° C. and potassium t-butoxide (3.55 g, 0.03 mol) was added. The mixture was stirred for ¼ hour and then isoamyl nitrite (2.90 g, 0.024 mol) was added dropwise over several minutes. After 1½ hours at −10° C., the reaction was poured into a cold mixture of ethyl acetate (100 ml), water (100 ml) and acetic acid (50 ml). Sodium bicarbonate was added to basify the mixture. The ethyl acetate solution was separated, washed with saturated NaCl, dried over $Na_2SO_4$, filtered and concentrated in vacuo to an amber oil (2.47 g).

(11) 3-Amino-2,3-dihydro-1-methyl-5-phenyl-1H-1,4-furo[3,2-e]diazepin-2-one

The 2,3-dihydro-1-methyl-3-oximido-5-phenyl-1H-1,4-furo[3,2-e]diazepin-2-one (2.56 g, 9.5 mmol) was dissolved in acetic acid (150 ml) and 5% palladium on carbon (2.0 g) was added under nitrogen. The mixture was hydrogenated under 10 PSIG of hydrogen for 3½ hours. The catalyst was filtered and the filtrate was concentrated in vacuo. The residual amber oil was neutralized with saturated $NaHCO_3$ (50 ml) and was extracted with ethyl acetate (150 ml in three portions). The extract was dried over $Na_2SO_4$, filtered and concentrated in vacuo to a viscous oil (1.58 g). Re-working the aqueous solutions gave more of the same oil (0.11 g). The product was purified by chromatography on silica gel using 10% methanol chloroform. Purified product was a yellow oil (1.14 g).

(12) N-[2,3-Dihydro-1-methyl-2-oxo-5-phenyl-1H-1,4-furo[3,2-e]diazepin-3-yl]-3-cyclohexylpropanamide 3-Amino-2,3-dihydro-1-methyl-5-phenyl-1H-1,4-furo[3,2-e] diazepin-2-one (255 mg, 1.0 mmol) and -3-cyclohexylpropionic acid (172 mg, 1.1 mmol) were dissolved in methylene chloride (5 ml) and dicyclohexylcarbodiimide (206 mg, 1.0 mmol) was added. The mixture was stirred at room temperature for 1 hour. The precipitated dicyclohexylurea was filtered and the filtrate was concentrated in vacuo to a pale yellow solid (444 mg). Silica gel chromatography using ethyl acetate gave a white solid (305 mg), mp 211°–214° C.

(13) N-[2,3-Dihydro-1-methyl-2-oxo-5-phenyl-1H-1,4-furo[3,2-e]diazepin-3-yl]-3-(2,4-dichlorophenyl)propanamide 3-Amino-2,3-dihydro-1-methyl-5-phenyl-1H-1,4-furo[3,2-e] diazepin-2-one (255 mg, 1.0 mmol) was dissolved in dry dimethylformamide (3 ml) under nitrogen. Then 3-(2,4-dichlorophenyl) propionic acid (219 mg, 1.0 mmol) was added followed by 1-ethyl-3-(3-dimethylaminopropyl)carbodiimide hydrochloride (288 mg, 1.5 mmol), 1-hydroxybenzotriazole hydrate (203 mg, 1.5 mmol) and triethylamine (152 mg, 1.5 mmol). The mixture was stirred at ambient temperature over night. The dimethylformamide was removed in vacuo and the residue was taken up in ethyl acetate (35 ml) and water (15 ml). The ethyl acetate was separated and was washed with 1.5N HCl and with water, dried over $Na_2SO_4$, filtered and concentrated in vacuo to a pale yellow solid (446 mg). Chromatography on silica gel using ethyl acetate gave 340 mg of product which was recrystallized from ethyl acetate. The white solid melted at 214°–215.5° C. (wt. 258 mg)

Other groups can be substituted for R simply by utilizing the appropriate carboxylic acid in the final step of the procedure.

Further exemplifying the novel compounds of this invention are those compounds where R is either

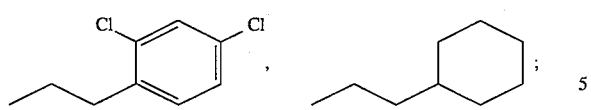
$R^1$ is t-butyl and $R^2$ is methyl. The preparation of compounds of this type is represented in Example II and shown schematically in Scheme II.
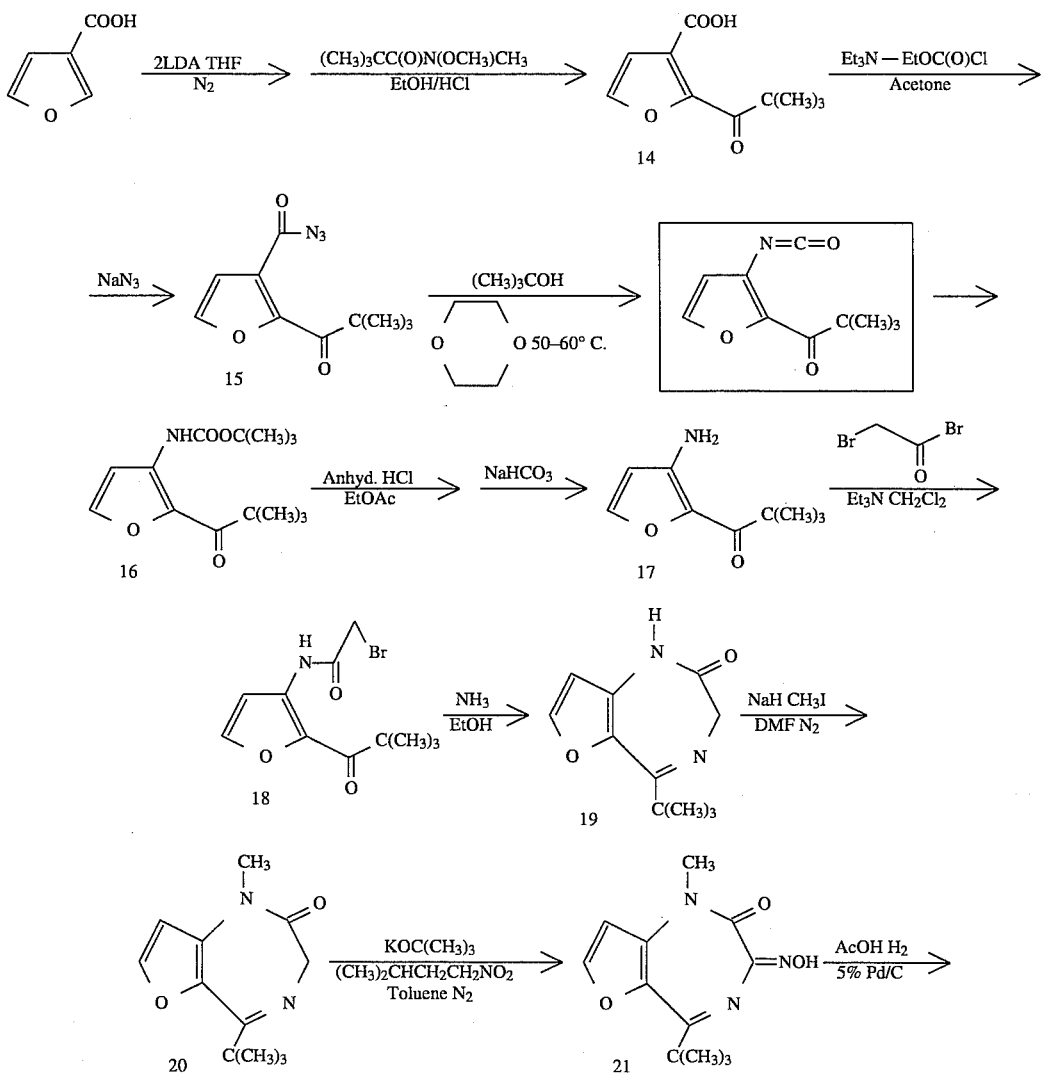

-continued
SCHEME II

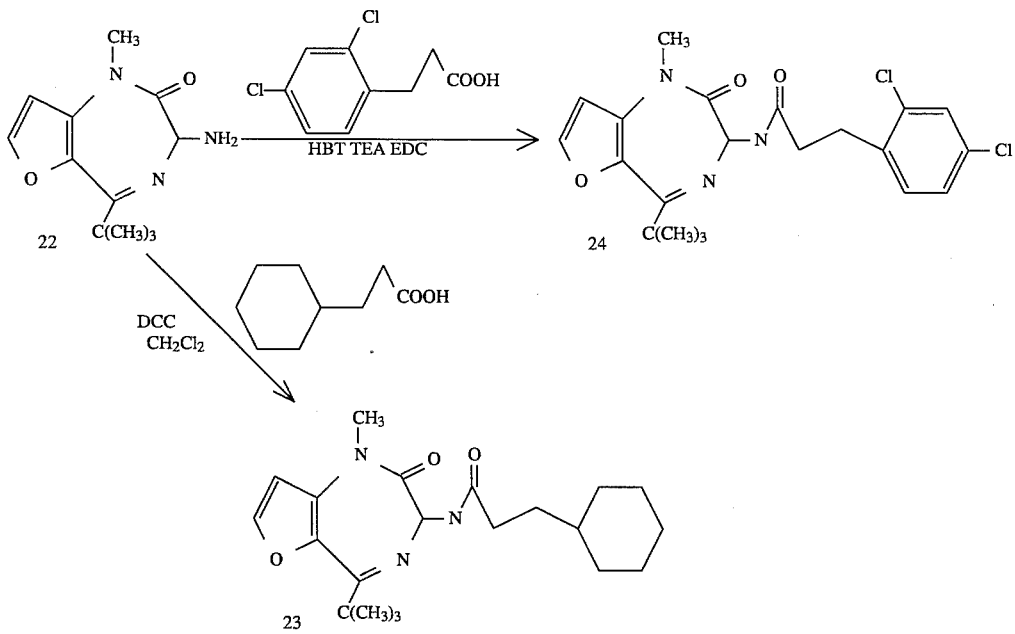

EXAMPLE II

(14) 2-Pivaloyl-3-furoic acid

A solution of 3-furoic acid (8.97 g, 0.08 mol) in tetrahydrofuran (200 ml) was cooled to −70° C. and a 2.0M solution of lithium diisopropylamide in THF-ethylbenzene-heptane (80 ml, 0.16 mol) was added dropwise over ¾ hr at −70° to −20° C. under nitrogen to give a tan suspension. A red solution formed after stirring for 1¾ hours at −20° C. To this solution was added N-methoxy-N-methylpivalamide (11.67 g, 0.08 mol) in tetrahydrofuran (10 ml) at −40° C. The reaction mixture was left at ambient temperature overnight. Then, it was cooled in ice and neutralized with 6N ethanolic hydrogen chloride (50 ml). The neutralized solution was acidified with 1.5N HCl (150 ml) and was extracted with ether (300 ml). The ether extracts were washed with saturated NaCl, dried over $Na_2SO_4$, filtered and concentrated in vacuo to a brown solid (15.4 g). Chromatography on silica gel using hexane-THF-acetic acid (10-2-0.2) gave a yellow solid (9.8 g), mp 85°–89° C.

(15) 2-Pivaloyl-3-furoyl azide

2-Pivaloyl-3-furoic acid (1.96 g, 0.01 mol) was dissolved in acetone (40 ml) and the solution was stirred at 0° C. under nitrogen. Triethylamine (1.7 ml, 0.012 mol) was added, followed by ethyl chloroformate (1.24 ml, 0.013 mol) and the mixture was stirred for 1½ hours. A solution of sodium azide (1.11 g, 0.017 mol) in water (4 ml) was added and the suspension was stirred for another 2 hours at 0° C. The solid was removed by filtration and the filtrate was diluted with water (25 ml). It was concentrated in vacuo to remove the acetone. The oil-water residue was extracted with ethyl acetate. The ethyl acetate extract was washed with saturated NaCl, dried over $Na_2SO_4$, filtered and concentrated to an amber oil (2.06 g) of 87% purity by HPLC.

(16) t-Butyl (2-pivaloylfuran-3-yl)carbamate

The 2-pivaloyl-3-furoyl azide (2.05 g, 0.01 mol) was dissolved in 1,4-dioxane (10 ml) and t-butyl alcohol (1.2 ml, 0.013 mol) was added. The solution was heated at 60° C. for 4½ hours, under nitrogen until the evolution of nitrogen ceased. Then, the dioxane was removed in vacuo and the residue was diluted with water (40 ml). The product was extracted into ethyl acetate (40 ml) and the extract was washed with saturated NaCl, dried over $Na_2SO_4$, filtered and concentrated in vacuo to an amber oil (2.17 g).

(17) 3-Amino-2-pivaloylfuran

A solution of t-butyl (2-pivaloylfuran-3-yl)carbamate (2.15 g, 8.0 mmol) in ethyl acetate (25 ml) was saturated With anhydrous hydrogen chloride gas at 0° C. The solution was stirred at ambient temperature for 5 hours. and then was evaporated to dryness in vacuo. The residual solid was taken up in ethyl acetate (50 ml) and saturated $NaHCO_3$ (20 ml). Additional solid $NaHCO_3$ was added to basify the mixture. The ethyl acetate extract was separated, washed with saturated NaCl, dried over $Na_2SO_4$, filtered and concentrated in vacuo to an amber liquid (1.34 g).

(18) 3-(2-Bromoacetamido)-2-pivaloylfuran

The 3-amino-2-pivaloylfuran (1.33 g, 8.0 mmol) was dissolved in methylene chloride (15 ml) under nitrogen and the solution was cooled to 0° C. Triethylamine (1.34 ml, 9.6 mmol) was added followed by 2-bromoacetyl bromide (1.94 g, 9.6 mmol) added dropwise over ¼ hour. The mixture was stirred at ambient temperature over night. The reaction was diluted with ethyl acetate (25 ml) and saturated NaCl (10 ml). The organic layer was separated, washed with saturated NaCl, dried over $Na_2SO_4$, filtered and concentrated in vacuo. A brown oil (2.18 g) was obtained in theoretical yield.

(19) 2.3-Dihydro-2-oxo-5-t-butyl-1H-1,4-furo[3,2-e]diazepine

Absolute ethanol (25 ml) was saturated with anhydrous ammonia at 0° C. and a solution of 3-(2-bromoacetamido)-2-pivaloylfuran (2.18 g, 8.0 mmol) in ethanol (5 ml) was added dropwise over 10 minutes. After 2½ hours the bromo compound had reacted to form the amine. The excess ammonia and ethanol were removed in vacuo. The residual oil-solid mixture was taken up in ethanol (25 ml) and 3 Å molecular sieves (2.5 g) were added. The mixture was heated at reflux under nitrogen for 96 hours to obtain the cyclized product. Chromatography gave 0.58 g of a pale yellow solid, mp 178°–182°.

(20) 2,3-Dihydro-1-methyl-2-oxo-5-t-butyl-1H-1,4-furo[3,2-e] diazepine

N-Methylation of 2,3-dihydro-2-oxo-5-t-butyl-1H-1,4-furo[3,2e]diazepine is accomplished using the procedure for compound 8 by substituting compound 19 in place of compound 8. The N-methylated structure 20 is isolated as described for the 5-phenyl analog.

(21) 2,3-Dihydro-1-methyl-3-oximido-5-t-butyl-1H-1,4-furo[3,2-e]diazepin-2-one

Preparation of the 3-oximido analog in the 5-t-butyl series is accomplished using the procedure of compound 9 when structure 9 is replaced with structure 20.

(22) 3-Amino-2,3-dihydro-1-methyl-5-t-butyl-1,4H-furo[3,2-e]diazepin-2-one

Reduction of the 3-oximido function to the 3-amino group in the 5-t-butyl series is done by catalytic hydrogenation using the procedure of compound 10 but replacing structure 10 with the corresponding 5-t-butyl analog 21.

(23) N-[2,3-Dihydro1-methyl-2-oxo-5-t-butyl-1H-1,4-furo[3,2-e] diazepin-3-yl]-3-cyclohexylpropanamide The desired 3-cyclohexylpropanamide in the 5-t-butyl series is obtained using the procedure for compound 12 or 13 and replacing compound 11 with the 5-t-butyl equivalent compound 22. If the procedure for compound 13 is used, the 3-(2,4-dichlorophenyl) propionic acid must be replaced with 3-cyclohexylpropionic acid.

(24) N-[2,3-Dihydro-1-methyl-2-oxo-5-t-butyl-1H-1,4-furo[3,2-e] diazepin-3-yl]-3-(2,4-dichlorophenyl)propanamide The 3-(2,4-dichlorophenyl)propanamide derivative in the 5-t-butyl series is obtained using the reaction of Example I, for preparing compound 11 when the intermediate 11 is replaced with compound 22, the corresponding 5-t-butyl equivalent. If the procedure for compound 12 is used, the 3-cyclohexylpropionic acid must be replaced with 3-(2,4-dichlorophenyl)propionic acid.

Again, other groups can be substituted for R simply by utilizing the appropriate carboxylic acid in the final step of the procedure.

Further exemplifying the novel compounds of this invention are those compounds where oxygen is in the 8 position of the furanodiazepine ring system:

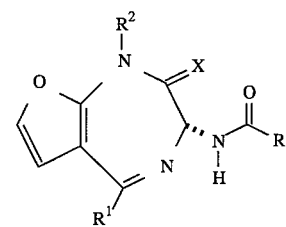

where R is either

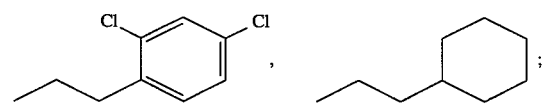

$R^1$ is phenyl, $R^2$ is methyl and X is O. The preparation of compounds of this type is presented in Example III and represented schematically in Scheme III.

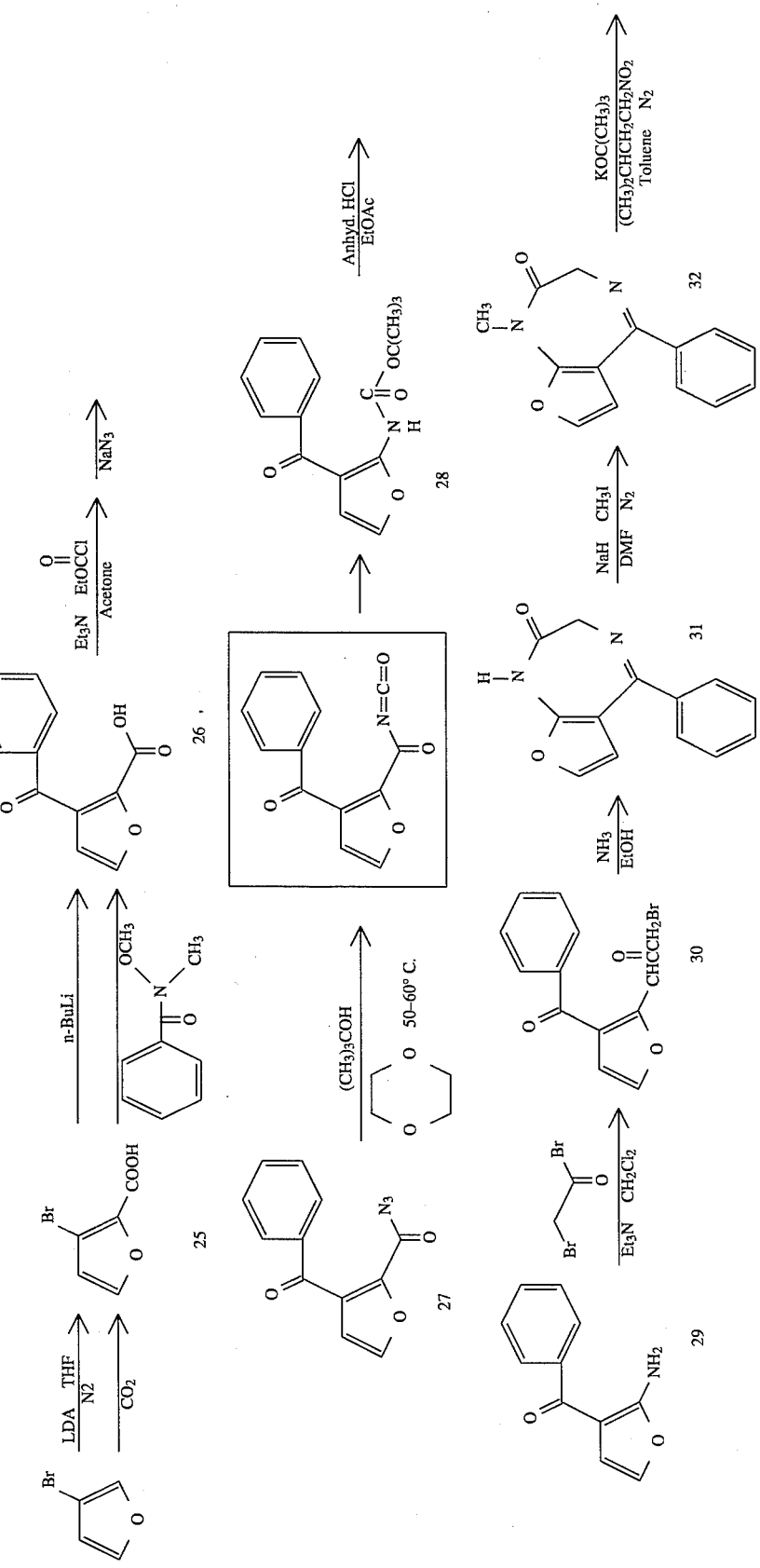

-continued
SCHEME III
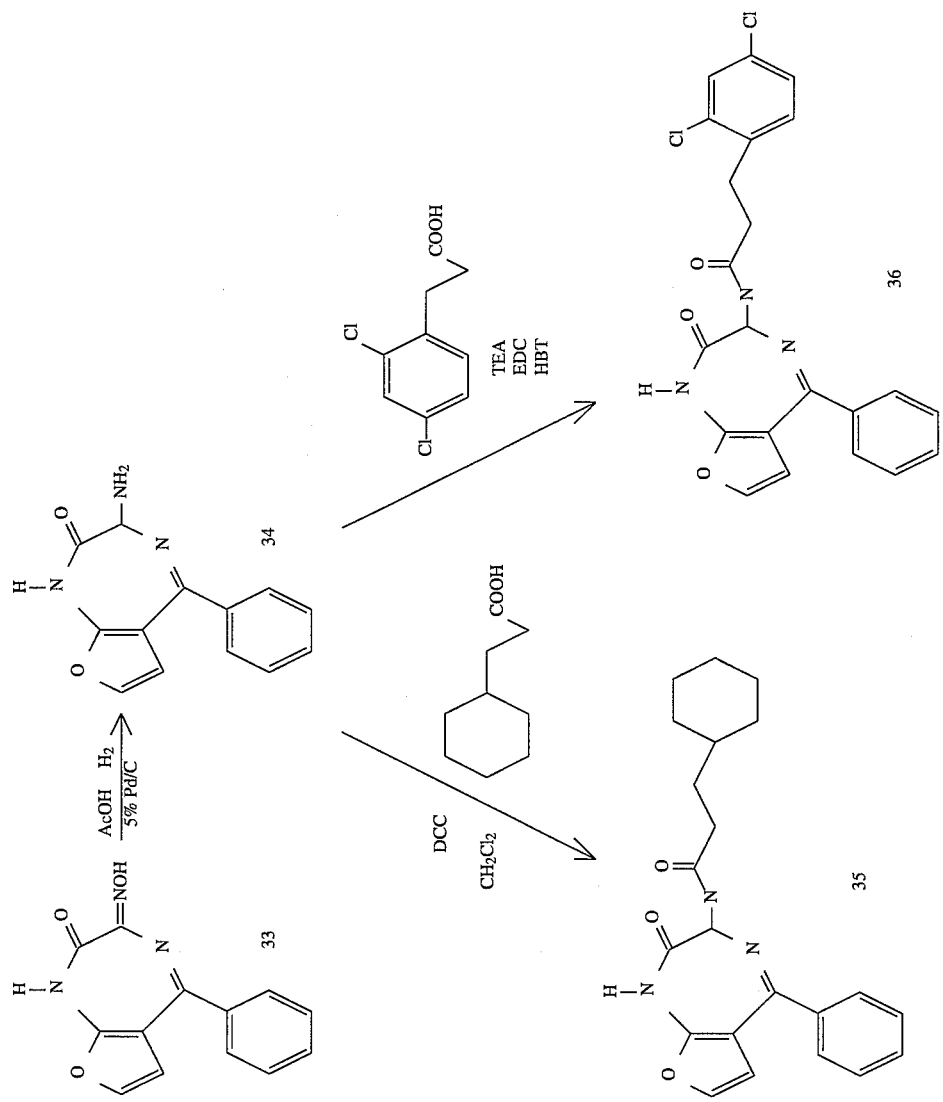

EXAMPLE III

(25) 3-Bromo-2-furoic acid

A solution of 3-bromofuran (14.7 g, 0.10 mol) in dry tetrahydrofuran (100 ml) was cooled to −78° C. under nitrogen and a 1.5M solution of lithium diisopropylamide in cyclohexane (73.3 ml, 0.11 mol) was added dropwise over ½ hour. The mixture was stirred at −78° C. for 2¼ hours. Then it was transferred under nitrogen to excess powdered dry ice with stirring and was left over night.

Water (100 ml) was added to dissolve the solid and the tetrahydrofuran was removed in vacuo. The aqueous residue was diluted with water (50 ml) and was washed with ether (2×50 ml). Then it was acidified with excess 6N HCl and was extracted with ethyl acetate (250 ml). The ethyl acetate extract was washed with saturated NaCl, dried over $Na_2SO_4$, filtered and concentrated in vacuo to a tan solid. Chromatography on silica gel using a mixture of hexane-THF-acetic acid (10-2-0.2) gave 11.47 g of 25.

(26) 3-Benzoyl-2-furoic acid

A solution of 3-bromo-2-furoic acid (1.91 g, 0.01 mol) in tetrahydrofuran (25 ml) was cooled to −78° C. Then a solution of 2.5M n-butyl lithium in hexane (8 ml, 0.02 mol) was added dropwise over 20 minutes under nitrogen. The resulting pale yellow suspension was stirred for 2 hours at −78° C.

N-Methoxy-N-methylbenzamide (1.82 g, 0.011 mol) in tetrahydrofuran (5 ml) was added dropwise over several minutes and the mixture was left at ambient temperature over night. The mixture was cooled in ice and 6N ethanolic hydrogen chloride (7 ml) was added. Tetrahydrofuran was removed in vacuo and the residue was taken up in ether (100 ml) and water (20 ml). The ether layer was washed with saturated NaCl, dried over $Na_2SO_4$, filtered and concentrated in vacuo to an oil. Chromatography on silica gel using a mixture of hexane-THF-acetic acid (10-3-0.2) gave a pale yellow solid 26 (1.34 g).

(27) 3-Benzoyl-2-furoyl azide

Using the procedure of Example I and replacing the 2-benzoyl-3-furoic acid, compound 2, with 3-benzoyl-2-furoic acid, compound 26, the corresponding acyl azide is prepared.

(28) t-Butyl (3-benzoylfuran-2-yl) carbamate

Decomposition of the acyl azide and rearrangement to the corresponding t-butylcarbamate is accomplished by heating in dioxane in the presence of t-butyl alcohol following the procedure for compound 4 in which compound 2 is replaced with compound 27.

(29) 2-Amino-3-benzoylfuran

Hydrolysis of the t-butylcarbamate according to the procedure for compounds 5 and 6 in which compound 28 is substituted for compound 4 gives the 2-amino-3-benzoylfuran, compound 29.

(30) 2-(2-Bromoacetamido)-3-benzoylfuran

2-Amino-3-benzoylfuran may be acylated with bromoacetyl bromide using the procedure for compound 7. When compound 6 is replaced in this procedure with compound 29 the title structure is obtained.

(31) 2,3-Dihydro-2-oxo-5-phenyl-1H-1,4-furo[2,3-e]diazepine

Amination of compound 30 and cyclization to the desired diazepine intermediate is carried out according to procedure for compound 8, by replacing compound 7 with compound 30.

(32) 2,3-Dihydro-1-methyl-2-oxo-5-phenyl-1H-1,4-furo[2,3-e] diazepin

Using the procedure described for the preparation of compound 9, the diazepine intermediate 31 may be N-methylated. Replacement of compound 8 with intermediate 31 gives the title structure.

(33) 2,3-Dihydro-1-methyl-3-oximido-5-phenyl-1H-1,4-furo[2,3-e] diazepine-2-one

Preparation of the 3-oximido analog 33 is accomplished using the reaction described for the preparation of compound 10, by replacing compound 9 with compound 32.

(34) 3-Amino-2,3-dihydro-1-methyl-5-phenyl-1H-1,4-furo[2,3-e] diazepine-2-one

Reduction of the oximido congener 33 is carried out catalytically according to the procedure for the preparation of compound 11. When compound 10 is replaced by compound 133 the penultimate amino intermediate 34 is obtained.

(35) N-[2,3-Dihydro-1-methyl-2-oxo-5-phenyl-1H-1,4-furo[2,3-e] diazepin-3-yl]-3-cyclohexylpropanamide

The desired 3-cyclohexylpropanamide is prepared by replacing compound 11 with compound 34 in a DCC acylation as described in the preparation of compound 12.

(36) N-[2,3-Dihydro-1-methyl-2-oxo-5-phenyl-1H-1,4-furo[2,3-e] diazepin-3-yl]-3-(2,4-dichloropheny)propanamide

Synthesis of the 3-(2,4-dichlorophenyl)propanamide from the amino intermediate 34 is best accomplished via the procedure for the preparation of compound 13. When compound 11 is replaced with structure 34 the title compound is obtained.

The term "heterocyclic" has been used throughout and referrs to those cyclic structures wherein atoms such as nitrogen, sulfur, oxygen and others, in addition to carbon, are used to construct the ring system. The term aryl refers to phenyl.

The novel compounds of the present invention, have the pharmacological properties required for antiarrhythmic agents of Class III, namely the prolongation of the myocardial action potential in vitro, without a significant depression of the Vmax, and the prolongation of QTc-interval in anesthetized dogs.

These compounds are effective in treating and preventing all types of arrhythmias including ventricular and atrial (supraventricular) arrhythmias. The compounds of the present invention are especially useful to control reentrant arrhythmias and prevent sudden death due to the ventricular fibrillation. These compounds are also effective in treating and preventing impaired cardiac pump functions.

In the novel method of this invention of treating arrhythmia, one of the compounds or pharmaceutically acceptable salt thereof, is administered in an mount ranging from about 0.0001 to about 20 mg per kg or body weight per day, preferably from about 0.001 to about 10 mg per kg of body weight per day in a single dose or in 2 to 4 divided doses.

These compounds can be administered as the sole active ingredient or in combination with other antiarrhythmic agents or other cardiovascular agents.

These compounds, or pharmaceutically acceptable salts thereof, in the described dosages, are administered orally, intraperitoneally, subcutaneously, intramuscularly, transdermally, sublingually or intravenously. They are preferably administered intravenously or orally, for example in the form of tablets, troches, capsules, elixirs, suspensions, syrups, wafers, chewing gum, or the like prepared by art recognized procedures. The amount of active compound in such therapeutically useful compositions or preparations is such that a suitable dosage will be obtained.

The activity of the compounds described herein as antiarrhythmic agents is measured by their ability to block the IKs and IKr as determined by the following test protocol.

Outward potassium currents are measured in single guinea pig ventricular myocytes using a whole-cell voltage clamp technique described in detail elsewhere (Sanguinetti and Jurkiewicz, 1990, two components of cardiac delayed actifier K+ current: differential sensitivity to block by Class III antiarrhythmic agents. *J. Gen Physiol.* 96: 195–215). Myocytes are isolated by enzymatic (collagenase and protease) digestion of Langandorf perfused hearts. Single cells are then voltage clamped using 1 mm square-bore pipettes filled with 0.5M Kgluconate, 25 mM KCl, 5 mM K (2)ATP. Cells are bathed in a solution containing, in mN: 132 NaCl, 4KCl, 1.2 MgCl[2], 10 HEPES, 10, glucose: pH 7.2, temp. 35° C.

Each cell is maintained at a holding potential of −50 mV. Test depolarizations are applied as voltage ramps from −85 to −50 mV, and as steps to −10 mV (0.5 s) and +50 mV (1.0 s). I[KI] is measured as peak outward current during the voltage ramp. I[Kr] is measured as tail currents upon repolarization from −10 mV to −50 mV. I[KS] is measured as time-dependent current during the pulse to +50 mV. Currents are measured during control, then after exposure to drug at two different concentrations.

Employing this test the compounds described herein have an $IC_{50}$ of less then 1000 nM as IKs and/or IKr blockers.

What is claimed is:

1. A compound of the structural formulae of I or II:

[Structure I]

[Structure II]

or a pharmaceutically acceptable salt, hydrate or crystal form thereof, the racemic mixture or the individual enantiomers, the diastereomeric mixture, pure diastereomer or enantiomers thereof wherein:

R is $C_1$ to $C_6$ alkyl, $C_1$ to $C_6$ alkylphenyl wherein the phenyl ring is unsubstituted or substituted with $C_1$–$C_6$ alkyl, $C_1$–$C_6$ alkoxy, hydroxy $C_1$–$C_6$ alkyl, $NR^5R^6$ $C_1$–$C_6$ alkyl, halo, $NR^5R^6$, or hydroxy; $C_1$–$C_6$ alkyl substituted with cycloalkyl $C_3$–$C_8$,

[Structure: dichlorophenylpropyl or cyclohexylpropyl]

$R^1$ is $C_1$ to $C_6$ alkyl, either straight or branched chain, $C_1$ to $C_6$ substituted alkyl, $C_1$ to $C_6$ alkyphenyl, phenyl, substituted phenyl wherein the phenyl ring is unsubstituted or substituted with $C_1$–$C_6$ alkyl, $C_1$–$C_6$ alkoxy, hydroxy, hydroxy $C_1$–$C_6$ alkyl, $NR^5R^6$ $C_1$–$C_6$ alkyl, halo, $NR^5R^6$;

$R^2$ is H, $C_1$ to $C_6$ alkyl, either straight or branched chain, or alkylamino;

X is O;

$R^3$ is unsubstituted $C_1$–$C_6$ alkyl, $C_1$–$C_6$ alkoxy, $NO_2$, cyano, COOH, or $COOC_1$–$C_6$ alkyl, $NR^5R^6$, or substituted $C_1$–$C_6$ alkyl wherein the substitution is hydroxy, $C_1$–$C_6$ alkoxy, $NR^5R^6$;

$R^5$ and $R^6$ are independently hydrogen or $C_1$–$C_6$ alkyl.

2. The compound of claim 1 selected from the group consisting of

[Structure]

where R is either

[Structure: dichlorophenylpropyl or cyclohexylpropyl]

$R^1$ is phenyl or t-butyl;

$R^2$ is methyl;

and X is O.

3. The compound of claim 1 selected from the group consisting of

[Structure]

where R is either

[Structure: dichlorophenylpropyl or cyclohexylpropyl]

$R^1$ is phenyl;

$R^2$ is methyl;

and X is O.

4. A pharmaceutical formulation comprising a pharmaceutically acceptable carrier and a therapeutically effective amount of the compound of claim 1 or a pharmaceutically acceptable salt thereof.

5. A method of preventing or treating arrhythmia which comprises the administration to a patient in need of such treatment of an antiarrhythmically effective amount of the compound of claim 1.

* * * * *